(12) United States Patent
Yang

(10) Patent No.: US 6,613,084 B2
(45) Date of Patent: Sep. 2, 2003

(54) STENT HAVING COVER WITH DRUG DELIVERY CAPABILITY

(76) Inventor: Jun Yang, 46 Foxtail La., Dove Canyon, CA (US) 92679

(*) Notice: Subject to any disclaimer, the term of this patent is extended or adjusted under 35 U.S.C. 154(b) by 0 days.

(21) Appl. No.: 09/997,072

(22) Filed: Nov. 28, 2001

(65) Prior Publication Data

US 2002/0062147 A1 May 23, 2002

Related U.S. Application Data

(63) Continuation-in-part of application No. 09/524,650, filed on Mar. 13, 2000, now Pat. No. 6,379,382.

(51) Int. Cl.[7] ................................................. A61F 2/06
(52) U.S. Cl. ...................................... 623/1.42; 623/1.13
(58) Field of Search ............................... 623/1.42–1.48, 623/1.13; 600/3

(56) References Cited

U.S. PATENT DOCUMENTS

| | | |
|---|---|---|
| 3,657,744 A | 4/1972 | Ersek |
| 3,988,782 A | 11/1976 | Dardik et al. |
| 4,140,126 A | 2/1979 | Choudhury |
| 4,925,710 A | 5/1990 | Buck et al. |
| 5,122,154 A | 6/1992 | Rhodes |
| 5,123,917 A | 6/1992 | Lee |
| 5,286,254 A | 2/1994 | Shapland et al. |
| 5,383,928 A * | 1/1995 | Scott et al. ................ 623/1.42 |
| 5,389,106 A | 2/1995 | Tower |
| 5,411,550 A | 5/1995 | Herweck et al. |
| 5,466,509 A | 11/1995 | Kowligi et al. |
| 5,507,771 A | 4/1996 | Gianturco |
| 5,562,697 A | 10/1996 | Christiansen |
| 5,562,728 A | 10/1996 | Lazarus et al. |
| 5,578,075 A * | 11/1996 | Dayton ...................... 623/1.42 |
| 5,584,877 A | 12/1996 | Miyake et al. |
| 5,609,629 A | 3/1997 | Fearnot et al. |
| 5,616,608 A | 4/1997 | Kinsella et al. |

(List continued on next page.)

FOREIGN PATENT DOCUMENTS

| | | |
|---|---|---|
| EP | 0646365 | 4/1995 |
| EP | 0657147 | 6/1995 |
| EP | 0667132 | 8/1995 |
| EP | 0714269 | 6/2000 |
| WO | 9501761 | 1/1995 |
| WO | 9509586 | 4/1995 |
| WO | WO 95/10989 | 4/1995 |
| WO | 9607371 | 3/1996 |
| WO | WO 97/24081 | 7/1997 |
| WO | WO 98/25545 | 6/1998 |
| WO | 9825546 | 6/1998 |
| WO | WO 98/31305 | 7/1998 |
| WO | WO 98/34669 | 8/1998 |
| WO | WO 98/56312 | 12/1998 |
| WO | WO 99/15104 | 4/1999 |
| WO | WO 99/27989 | 6/1999 |
| WO | WO 99/38455 | 8/1999 |
| WO | WO 00/09041 | 2/2000 |
| WO | WO 00/12147 | 3/2000 |
| WO | WO 01/15633 | 3/2000 |
| WO | WO 00/18328 | 4/2000 |
| WO | WO 00/33768 | 6/2000 |
| WO | WO 00/42949 | 7/2000 |
| WO | WO 00/48530 | 8/2000 |
| WO | WO 00/49973 | 8/2000 |
| WO | WO 00/50116 | 8/2000 |
| WO | WO 01/26707 | 4/2001 |
| WO | WO 01/67992 | 9/2001 |

*Primary Examiner*—David H. Willse
*Assistant Examiner*—Suzette J. Jackson
(74) *Attorney, Agent, or Firm*—Raymond Sun (57) ABSTRACT

A prosthesis has a stent, and a cover that covers a portion of the stent. The cover has at least two layers of materials that can define at least one chamber therebetween, with a drug loaded into the at least one chamber by a dug dispersing element. The cover can be provided inside the luminal walls of the stent, or the stent can be retained in the at least one chamber. The cover can also be deployed to treat vulnerable plaque.

15 Claims, 7 Drawing Sheets

U.S. PATENT DOCUMENTS

| | | | |
|---|---|---|---|
| 5,620,763 A | | 4/1997 | House et al. |
| 5,628,784 A | | 5/1997 | Strecker |
| 5,628,788 A | | 5/1997 | Pinchuk |
| 5,637,113 A | | 6/1997 | Tartaglia et al. |
| 5,643,309 A | * | 7/1997 | Myler et al. .................. 606/91 |
| 5,674,241 A | | 10/1997 | Bley et al. |
| 5,693,085 A | * | 12/1997 | Buirge et al. .............. 623/1.47 |
| 5,697,967 A | * | 12/1997 | Dinh et al. ................. 623/1.42 |
| 5,700,285 A | | 12/1997 | Myers et al. |
| 5,700,286 A | | 12/1997 | Tartaglia et al. |
| 5,707,385 A | | 1/1998 | Williams |
| 5,709,874 A | | 1/1998 | Hanson et al. |
| 5,718,973 A | | 2/1998 | Lewis et al. |
| 5,723,004 A | | 3/1998 | Dereume et al. |
| 5,725,567 A | | 3/1998 | Wolff et al. |
| 5,733,302 A | | 3/1998 | Myler et al. |
| 5,735,892 A | | 4/1998 | Myers et al. |
| 5,735,897 A | | 4/1998 | Buirge |
| 5,769,883 A | | 6/1998 | Buscemi et al. |
| 5,779,732 A | | 7/1998 | Amundson |
| 5,788,626 A | * | 8/1998 | Thompson .................. 600/36 |
| 5,843,166 A | | 12/1998 | Lentz et al. |
| 5,857,998 A | | 1/1999 | Barry |
| 5,865,723 A | | 2/1999 | Love |
| 5,873,904 A | | 2/1999 | Ragheb et al. |
| 5,876,432 A | | 3/1999 | Lau et al. |
| 5,897,589 A | | 4/1999 | Cottenceau et al. |
| 5,902,332 A | | 5/1999 | Schatz |
| 5,925,074 A | | 7/1999 | Gingras et al. |
| 5,925,075 A | | 7/1999 | Myers et al. |
| 5,941,895 A | * | 8/1999 | Myler et al. ................. 606/195 |
| 5,948,018 A | | 9/1999 | Dereume et al. |
| 5,951,586 A | | 9/1999 | Berg et al. |
| 5,957,974 A | | 9/1999 | Thompson et al. |
| 5,961,545 A | | 10/1999 | Lentz et al. |
| 5,968,070 A | | 10/1999 | Bley et al. |
| 5,980,565 A | | 11/1999 | Jayaraman |
| 5,990,379 A | | 11/1999 | Gregory |
| 6,013,099 A | | 1/2000 | Dinh et al. |
| 6,099,562 A | * | 8/2000 | Ding et al. ................. 623/1.46 |
| 6,117,166 A | | 9/2000 | Winston et al. |
| 6,139,573 A | | 10/2000 | Sogard et al. |
| 6,156,064 A | * | 12/2000 | Chouinard ................. 623/1.44 |
| 6,187,039 B1 | * | 2/2001 | Hiles et al. ................ 623/1.44 |
| 6,193,746 B1 | * | 2/2001 | Strecker .................... 623/1.13 |
| 6,206,914 B1 | * | 3/2001 | Soykan et al. ............. 623/1.42 |
| 6,206,915 B1 | * | 3/2001 | Fagan et al. ............... 623/1.42 |
| 6,214,039 B1 | | 4/2001 | Banas et al. |
| 6,218,016 B1 | | 4/2001 | Tedeschi et al. |
| 6,231,614 B1 | | 5/2001 | Yang et al. |
| 6,248,122 B1 | | 6/2001 | Klumb et al. |
| 6,254,627 B1 | | 7/2001 | Freidberg |
| 6,309,413 B1 | * | 10/2001 | Dereume et al. .......... 623/1.13 |
| 6,358,284 B1 | * | 3/2002 | Fearnot et al. ........... 623/23.72 |
| 6,398,788 B1 | * | 6/2002 | Jacobsen et al. ........... 623/1.42 |
| 6,447,439 B1 | * | 9/2002 | Vallana et al. ................. 600/3 |
| 6,461,644 B1 | * | 10/2002 | Jackson et al. ............. 424/499 |

\* cited by examiner

STENT HAVING COVER WITH DRUG DELIVERY CAPABILITY

RELATED CASES

This is a continuation-in-part of Ser. No. 09/524,650 filed on Mar. 13, 2000, now U.S. Pat. No. 6,379,382 entitled "Stent Having Cover with Drug Delivery Capability", the entire disclosure of which is incorporated by this reference as though set forth fully herein.

BACKGROUND OF THE INVENTION

1. Field of the Invention

The present invention relates to prostheses for implantation into a mammalian vessel, and in particular, to intraluminal stents that are provided with a cover that can deliver and release drugs.

2. Description of the Prior Art

The treatment of stenosis is the subject of much research and discussion. Stenosis are currently being treated by a number of well-known procedures, including balloon dilatation, stenting, ablation, atherectomy or laser treatment.

Restenosis is the renarrowing of a peripheral or coronary artery after trauma to that artery caused by efforts to open a stenosed portion of the artery, such as by balloon dilatation, ablation, atherectomy or laser treatment of the artery. For such procedures, restenosis occurs at a rate of about 20–50% depending on the definition, vessel location, lesion length and a number of other morphological and clinical variables. Restenosis is believed to be a natural healing reaction to the injury of the arterial wall that is caused by angioplasty procedures. The host reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

Many attempts have been made or suggested to treat stenosis, and to prevent or minimize restenosis. One common approach is to implant intravascular stents in coronary and peripheral vessels. The stent is usually inserted by a delivery system (e.g., such as a catheter) into a vascular lumen and expanded (either via a balloon on a catheter, or through self-expansion) into contact with the diseased portion of the arterial wall to provide mechanical support for the lumen. The positioning of the stent in the lumen can be used to treat stenosis by re-opening the lumen that had been partially blocked by the stenosis. However, it has been found that restenosis can still occur with such stents in place. In addition, a stent itself can cause undesirable local thrombosis. To address the problem of thrombosis, persons receiving stents also receive extensive systemic treatment with anticoagulant and antiplatelet drugs.

To address the restenosis problem, a number of approaches have been suggested. One type of approach relates to the delivery of drugs to minimize restenosis. As one example, these drugs can be delivered via oral, intravascular or intramuscular introduction, but these attempts have been largely unsuccessful. Unfortunately, pills and injections are known to be ineffective modes of administration because constant drug delivery and higher local concentration are very difficult to achieve via these means. Through repeated doses, these drugs often cycle through concentration peaks and valleys, resulting in time periods of toxicity and ineffectiveness.

Localized drug delivery is another example. There were many different attempts to provide localized drug delivery. One example of localized drug delivery is to provide the metallic walls or wires of the stents with therapeutic substances, fibrin and other drugs that can be released over a period of time at the diseased location of the vessel. However, the incorporation of drugs into the walls or wires of the stent may significantly compromise the strength of the stent.

A second example of localized drug delivery is to incorporate a drug into a stent that is constructed not of metal but of a biodegradable polymer. However, the loading in and releasing of drugs from a polymeric stent may change the structural integrity and mechanical properties of the stent.

A third example of localized drug delivery is to directly coat the metal stent with a polymer that is bonded to or contains the desired drugs or anti-stenotic substances. Unfortunately, such polymer-coated stents have not been completely effective in preventing restenosis because of the cracking of the polymer as the stent is being expanded during deployment, saturation of the drug binding sites on the stent, and other reasons.

A fourth example of localized drug delivery is to provide a polymer sleeve or sheath that encompasses a portion of the stent. The sleeve or sheath would operate as a local drug delivery device. In some instances, the sheath or sleeve is made up of a bioabsorbable polymer that incorporates a drug, with the sheath or sleeve having a thickness to allow for controlled release of the drug. However, this approach suffers from the drawback that very few drugs are capable of being incorporated with common solid state polymers. In addition, directional release of drug to either the lumen or the arterial wall cannot be achieved. It will also be problematic for medical practitioners to select the type of drug and the dosage of the drug to be used, as well as the stent type to be implanted.

In addition to the problems of stenosis and restenosis, the development of cancerous blockages inside body passageways (e.g., esophagus, bile ducts, trachea, intestine, vasculature and urethra, among others) can also be treated with stents, which operate to hold open passageways which have been blocked by the cancerous growth or tumors. However, the stents do not prevent the ingrowth of the cancerous material through the interstices of the stent. If the ingrowth reaches the inside of the stent, it might result in blockage of the body passageway in which the stent had been implanted.

In addition to the above-described problems experienced by localized drug delivery, conventional stents are also ineffective in preventing the ingrowth of host tissue proliferation or inflammatory material through the interstices of the stent. Some inflammatory reactions may be associated with vulnerable plaque or other unknown causes.

Traditional scientific wisdom holds that heart attacks originate from severe blockages created by atherosclerosis (i.e., the progressive build-up of plaque in the coronary arteries). The increase of lipids in the artery and the ensuing tissue reaction lead to narrowing of the affected vessel which, in turn, can result in angina and eventual coronary occlusion, sudden cardiac death, and thrombotic stroke. However, research conducted in the past decade is leading to a shift in understanding of atherosclerosis and pointing the way to major changes in the diagnosis and treatment of some kinds of life threatening forms of heart disease.

Scientists theorize that at least some coronary diseases are inflammatory processes, in which inflammation causes plaque to rupture. These so-called "vulnerable plaques" do not block the arteries. On the other hand, much like an abscess, they are ingrained under the arterial wall, so that they are undetectable. They cannot be seen by conventional angiography or fluoroscopy, but they cause symptoms such as shortness of breath or pain. Yet, for a variety of reasons, they are more likely to erode or rupture, creating a raw tissue surface that forms scabs. Thus, they are more dangerous than other plaques that cause pain, and may be responsible for as much as 60–80% of all heart attacks.

As used herein, the term "restenosis" is defined to be a natural healing reaction to the injury of the arterial wall that is caused by angioplasty procedures. "Restenosis" is not associated with vulnerable plaque. The host reaction begins with the thrombotic mechanism at the site of the injury. The final result of the complex steps of the healing process can be intimal hyperplasia, which is the uncontrolled migration and proliferation of medial smooth muscle cells, combined with their extracellular matrix production, until the artery is again stenosed or occluded as typically observed in a stable plaque as opposed to a vulnerable plaque.

Thus, there still remains a need for a prosthesis that provides effective localized drug delivery to minimize or prevent restenosis and the ingrowth of host tissue proliferation or inflammatory material through the interstices of the stent, while avoiding the disadvantages set forth above. In addition, there remains a clinical need for a method for treating vulnerable plaque.

SUMMARY OF THE DISCLOSURE

It is an object of the present invention to provide an intraluminal prosthesis that minimizes or prevents the ingrowth of host tissue proliferation or inflammatory material through the interstices or ends of a stent.

It is another object of the present invention to provide an intraluminal prosthesis that provides effective localized drug delivery.

It is yet another object of the present invention to provide an intraluminal prosthesis that provides site-specific drug delivery and/or evenly distributed drug delivery for treating a region of the intraluminal surface.

It is yet a further object of the present invention to provide a method for treating vulnerable plaque.

In order to accomplish the objects of the present invention, there is provided a prosthesis having a stent, and a cover that covers a portion of the stent. The cover has at least two layers of materials. In one embodiment of the present invention, the layers of material define at least one chamber therebetween, and a drug is loaded into the chamber by a drug dispersing element. In another embodiment of the present invention, the drug can be loaded into the material of one or more layers. The cover can be provided inside the luminal walls of the stent, or the stent can be retained in the at least one chamber. The cover of the present invention can be deployed to treat vulnerable plaque.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides an intraluminal prosthesis that has an underlying stent with a cover acting as a sheath, patch, or sleeve. The cover acts as a drug delivery device for locally delivering a drug to a vessel wall or lumen into which the prosthesis has been inserted and positioned. The cover also functions to block the path of cell migration (i.e., ingrowth), and to pave or act as a scaffold for supporting the lumen, such as in stenosis, restenosis, tumorous, or vulnerable plaque treatment. The cover also functions to treat vulnerable plaque.

The cover of the present invention can be provided in the form of a tubular cover or patch. The tubular cover or patch cover can be generally made of a biocompatible material that is also referred to as a "biomaterial". The patch may be secured to a portion of the outer periphery of the stent by gluing, stitching, adhering, stapling, suturing, or other means, as described in greater detail hereinbelow.

When embodied as a tubular cover, the cover of the present invention can, in one example, be configured as a seamless tubing. A seamless tubing is essentially a tubing that does not have any seam or crease or fold, and examples include an extruded hollow tubing or a blood vessel. A seamless tubing can be configured for maintaining the stretchably distensible pressure to be essentially uniform over the circumference of the cover.

The prosthesis of the present invention may comprise a cover provided about a portion or all of a tubular stent. The stent according to the present invention can be any stent, including a self-expanding stent, or a stent that is radially expandable by inflating a balloon, or expanded by an expansion member, or a stent that is expanded by the use of radio frequency which provides heat to cause the stent to change its size. The stent can also be made of any desired material, including a metallic material, a metal alloy (e.g., nickel-titanium) or even polymeric composites. The stent can have any wire or cell design, as described below. Examples of self-expanding wire mesh stents that can be used include the coronary Wallstent™ marketed by Schneider, and the SciMED Radius™ stent marketed by Boston Scientific Corp. Examples of balloon expandable stents that can be used include the Multilink™ stent by Guidant Corp., the Coronary Stent S670 by Medtronic AVE, the Nir™ stent by Boston Scientific Corp., the Cross Flex™ stent by Cordis, the PAS™ stent by Progressive Angioplasty Systems Inc., the V-Flex Plus™ stent by Cook, Inc., and the Palmaz-Schatz™ Crown and Spiral stents by Cordis, among others. The vessels in which the stent of the present invention can be deployed include but are not limited to natural body vessels such as ducts, arteries, trachea, veins, intestines, bile ducts, ureters and the esophagus.

The term "drug" as used herein is intended to mean any compound which has a desired pharmacologic effect. The drug should be compatible with the cover and can be tolerated in a patient. For example, the drug can be an anticoagulant, such as an RGD peptide-containing compound, heparin, antithrombin compounds, platelet receptor antagonists, anti-thrombin antibodies, anti-platelet receptor antibodies, aspirin, protaglandin inhibitors, platelet inhibitors, or tick anti-platelet peptide. The drug can also be a promoter of vascular cell growth, such as a growth factor receptor antagonists, transcriptional activator or translational promoter. Alternatively, the drug can be an inhibitor of vascular cell growth, such as a growth factor inhibitor, growth factor receptor antagonists, transcriptional repressor or translational repressor, antisense DNA, antisense RNA, replication inhibitor, inhibitory antibodies, antibodies directed against growth factors, and bifunctional molecules. The drug can also be a cholesterol-lowering agent, a vasodilating agent, and agents which interfere with endogenous vasoactive mechanisms. Other examples of drugs can include anti-inflammatory agents, anti-platelet or fibrinolytic agents, anti-neoplastic agents, antiallergic agents, anti-rejection agents, anti-microbial or anti-bacterial or anti-viral agents, hormones, vasoactive substances, anti-invasive factors, anti-cancer drugs, antibodies and lymphokines, anti-angiogenic agents, radioactive agents and gene therapy drugs, among others. The drug may be loaded as in its/their original commercial form, or together with polymer or protein carriers, to achieve delayed and consistent release.

Specific non-limiting examples of some drugs that fall under the above categories include paclitaxel, docetaxel and derivatives, epothilones, nitric oxide release agents, heparin, aspirin, coumadin, PPACK, hirudin, polypeptide from angiostatin and endostatin, methotrexate, 5-fluorouracil, estradiol, P-selectin Glycoprotein ligand-1 chimera, abciximab, exochelin, eleutherobin and sarcodictyin, fludarabine, sirolimus, tranilast, VEGF, transforming growth factor (TGF)-beta, Insulin-like growth factor (IGF), platelet derived growth factor (PDGF), fibroblast growth factor (FGF), RGD peptide, beta or gamma ray emitter (radioactive) agents.

The cover can be made from either a tissue, a hydrogel, or a polymer, as these terms are defined hereinbelow. The tissues and hydrogels according to the present invention should have a high water content and be able to absorb fluids (i.e., liquid drugs, or drugs carried in fluids).

The term "tissue" as used herein is intended to mean any mammalian (human or animal) tissue that has sufficient strength and elasticity to act as the primary component of the prosthesis. Tissue can have a cellular matrix of proteins (e.g., collagen). Tissue can include tissue that is obtained from the host patient in which the prosthesis is to be implanted (known as autologous tissue). Tissue can also include homologous tissue, such as from cadavers, umbilical cords, and placenta. In addition, tissue can include heterologous tissue, such as from swine, canine, sheep, horse, etc. Tissue can also include tissue produced in vitro using cell culture methods. In one embodiment of the present invention, luminal tissues (e.g., venous tissue such as saphenous veins, antecubital vein, cephalic vein, omental vein, mesentric vein) are preferred. The tissue can be chemically cross-linked (e.g., by glutaraldehyde, polyepoxy, PEG, UV, etc.) or not chemically cross-linked (e.g., fresh, frozen or cryopreserved). The tissue can also be chemically modified with proper charge and hydrophilicity. The tissue can be harvested according to known techniques, such as those described in Love, *Autologous Tissue Heart Valves*, R.G. Landes Co., Austin, Tex., 1993, Chapter 8. The tissue material can be a mammalian vein that is stretchable radially by at least one and a half times the original circumference of the vein. In one embodiment, the tissue material can be a porcine vein which may be derived from an abdominal region that has little bifurcation.

Tissue as defined herein can even include tissue that has been processed under the techniques described in U.S. Pat. Nos. 6,106,555 and 6,231,614, whose complete disclosures are incorporated by this reference as though set forth fully herein. These patents disclose a chemical treatment method for tissue fixation and modification by using an epoxy compound. The epoxy compound has a hydrocarbon backbone that is devoid of either an ether or ester linkage. The epoxy compound can also be water-soluble. Thus, tissue may comprise cross-linked tissue or a vein, as these are disclosed in U.S. Pat. Nos. 6,106,555 and 6,231,614. Depending on the embodiment, a vein of porcine, bovine or other mammal origin procured from a slaughterhouse may be chemically treated and used as a stent cover of the present invention. The porcine or bovine vein can be derived from an abdominal region. The mammal vein is particularly applicable because of its stretchability. The stretchability of the stent cover is preferably in the range of 1½ to 6 times and beyond. More preferably, the stretchability is in the range of at least twice of its original circumference or original diameter. A tubular cover that is made of a chemical modified seamless tissue using an epoxy compound devoid of either an ether or ester linkage is particularly well adapted for use as a stent cover of the present invention.

The epoxy compound modified tissue for use as the cover of the present invention is biocompatible and retains essentially most of the original tissue compliance and strength. In contrast, using a tissue material without chemical modification as a stent cover tends to pose concerns in terms of antigenicity and enzymatic degradation. For example, a tissue chemically modified by a conventional glutaraldehyde treatment process is cytotoxic to the host tissue and is much less compliant than the pre-modified tissue.

Tissue as defined herein can even include tissue that is described in application Ser. No. 09/755,818, filed Jan. 15, 2001 by the present inventor and entitled *Vascular Tissue Composition*, whose complete disclosure is incorporated by this reference as though set forth fully herein. Application Ser. No. 09/755,818 discloses a tissue composition comprising a subendothelial layer, an elastica interna, and at least a portion of a tunica media of a blood vessel harvested from a mammal. The tissue composition comprising a subendothelial layer, an elastica interna, and at least a portion of a tunica media of a blood vessel may also be chemically treated, such as by glutaraldehyde, formaldehyde, dialdehyde starch, or by the epoxy compound disclosed in U.S. Pat. Nos. 6,106,555 and 6,231,614.

The modified tissue composition as disclosed in patent application Ser. No. 09/755,818 is particularly suitable as a stent cover of the present invention because it retains adequate strength to be mounted on an expanded stent while the modified tissue composition provides improved stretchability, and a lower profile because part of the tunica and/or adventitial layer is removed in the modified tissue composition. Further, the modified tissue composition may be chemically modified by epoxy compound as disclosed in U.S. Pat. Nos. 6,106,555 and 6,231,614 to yield a biocompatible stent cover that maintains essentially most of the original tissue compliance and strength.

A tubular stent cover configured for drug storage can include at least two layers of tissue material. According to one embodiment, at least one of the layers of tissue material is permeable to drugs, or the stent cover can have at least one perforation through which drugs can be passed.

The term "hydrogel" as used herein is intended to mean a natural gel-like material. Hydrogel can have a polymeric matrix of proteins or polymers. Depending on the material selected, the hydrogel material may have a proper hydrophilicity to regulate the water and drug diffusion process. Hydrogel can be synthetic polymer, such as polymalic acid, polyamino acids, polyacrylic acids, polyethylene glycol, polyvinylpyrrolidone, polyvinyl alcohols, and hydrophilic polyurethanes. Hydrogel can include albumin, collagen, gelatin, starch, celluloses, dextran, polymalic acid, polyamino acids and their co-polymers or lightly cross-linked forms. Other possible materials are polysaccharides and their derivatives. Yet other possible materials include sodium alginate, karaya gum, gelatin, guar gum, agar, algin, carrageenans, pectin, locust bean gums, xanthan, starch-based gums, hydroxyalkyl and ethyl ethers of cellulose, sodium carboxymethylcellulose. Some are food gels and some are bioadhesives.

The term "polymer" as used herein means any polymeric material, such as polyurethanes, expanded PTFE, PTFE, polyesters, polyamides, polylactide, polylactide-co-glycolide, polydioxanone, thermoplastic elastomers, thermoplastics, and silicone rubbers.

The term "material" as used herein means either tissue, hydrogel, or polymer.

Figure 1:
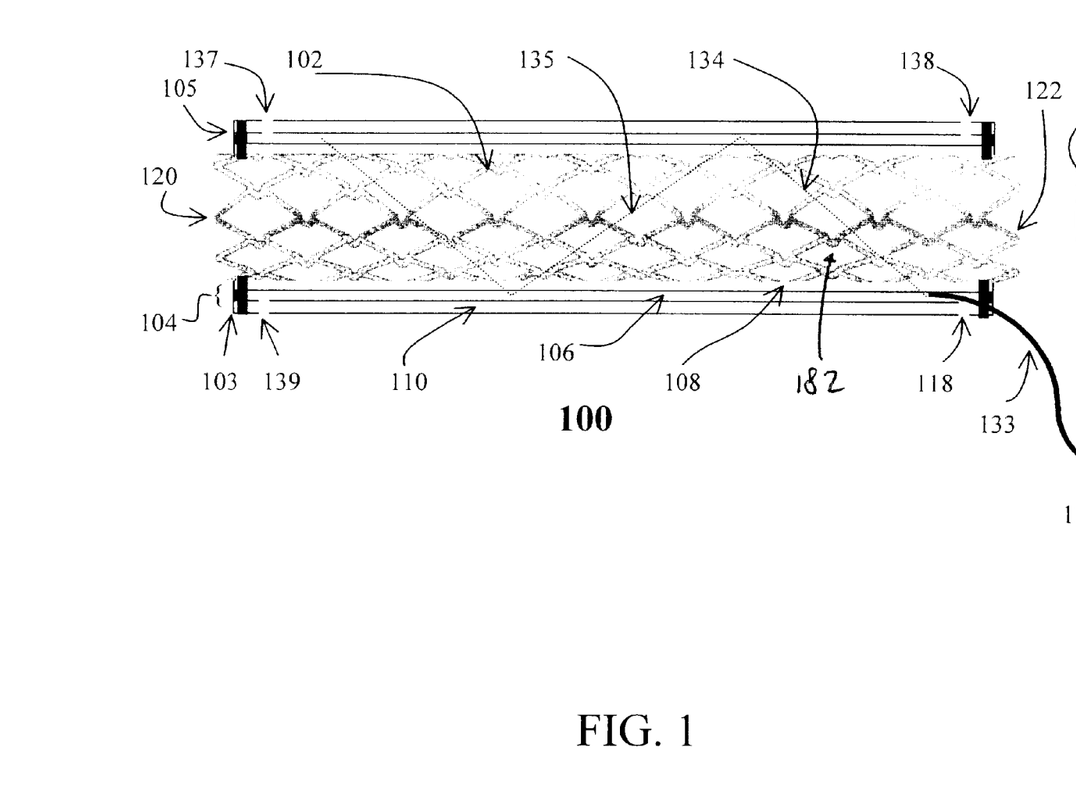
FIG. 1 is a schematic view of an intraluminal prosthesis according to one embodiment of the present invention.
Figure 2:
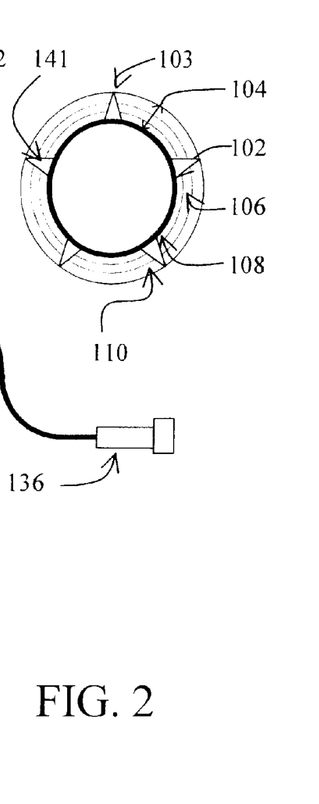
FIG. 2 is a cross-sectional view of the prosthesis of FIG. 1.

FIGS. 1 and 2 illustrate a prosthesis 100 according to one embodiment of the present invention. The prosthesis 100 has a tubular stent 102 and a cover 104 attached over the outer periphery of the stent 102. As described above, the stent 102 can be any known or conventional stent, and as a non-limiting example, FIG. 1 illustrates the stent 102 as being a self-expanding Nir™ stent by Boston Scientific Corp., as described in FIG. 8 of U.S. Pat. No. 5,733,303 to Israel et al., whose disclosure is incorporated herein as though fully set forth herein.

The cover 104 acts as a drug reservoir that stores the drug(s) to be released at the site of implantation of the prosthesis 100. The cover 104 is extensible (i.e., can be stretched) and flexible. The cover 104 defines a chamber or reservoir 106 that holds the drug(s) to be released. In the embodiment shown in FIGS. 1 and 2, the cover 104 has two physically separate layers of material 108 and 110 that define the chamber 106 therebetween. The cover 104 is formed by sealing the edges (e.g., by bioadhesive, laminating, welding, stapling, gluing, suturing or stitching) of the two layers 108 and 110 to form the chamber 106. As an alternative, the cover 104 can be formed by securing the two layers 108, 110 at one or more points that are offset from their edges. As a further alternative, the layers 108 and 110 can be sequentially mounted over the stent 102. Each layer 106 and 108 can be either a tissue, hydrogel, or polymer, as defined hereinabove. In addition, the separate layers 108 and 110 can be made of the same or different materials.

At least one of the layers 108, 110 should be a drug permeable layer to allow the drug(s) stored in the chamber 106 to be released. Tissue and hydrogel are generally water permeable, and polymer can be porous or non-porous. Water and molecules can diffuse through the permeable layers 108 and/or 110 at different rates. The diffusion rate can be controlled by varying the thickness of the layer, changing the size of the migrating molecules (either the drug alone or with a carrier to form a larger molecule to slow down the diffusion process), changing the hydrophilicity of the layer, changing the drug concentration (i.e., drug released from its polymeric carrier), and coating the surface of the layer with polymeric material having different permeability. The separate layers 108, 110 can also have different drug permeabilities. By varying the drug permeability of the layers 108, 110, a desired drug release rate can be achieved. For example, a high drug permeability for inner layer 108 will deliver most of the drug to the stent 102 and internal passageway instead of the vessel wall.

The cover 104 can be attached to the stent 102 by suturing the ends 103 of the cover 104 to the desired portions of the stent 102. For example, the cover 104 can be the same length as the stent 102, in which the ends 103 of the cover 104 are sutured (e.g., see suture 105 in FIG. 1) to the ends 120, 122 of the stent 102. If the length of the cover 104 is less than the length of the stent 102, then the ends 103 of the cover 104 can be sutured to selected wires of the stent 102 so that the cover 104 covers a portion of the stent 102. In an alternate embodiment, the cover 104 can be a patch to cover a non-continuous portion of the outer periphery of the stent 102. Other methods of attachment include the use of hooks or barbed mechanisms on the stent 102 to hook the cover 104 to the stent 102, or the use of glue to attach selected portions of the cover 104 to selected portions of the stent 102.

The cover 104 can be provided in the form of a tubular and seamless cover (i.e., luminal) or as a double-sheet that can be formed into a tubular cover by suturing or stitching side edges of the double-sheet. If the cover 104 is luminal, the cover 104 can be slid over the stent 102 and then attached. If the cover 104 is provided in the form of two attached sheets of material, the two sheets of material can be wrapped around the stent 102, and then attached. In either case, the attachment can be done with the stent 102 in the expanded state or in the compressed state. If the attachment is done in the expanded state, the prosthesis 100 is then compressed to a smaller diameter for delivery. When the prosthesis 100 is compressed, the flexible and stretchable nature of the cover 104 would allow the cover 104 to compress with the stent 102 without any creasing. Similarly, if the attachment is done in the compressed state, the flexible and stretchable nature of the cover 104 would allow the cover 104 to expand (e.g., stretch) with the expanding stent 102 when the prosthesis 100 is expanded.

As shown in FIG. 1, a drug-dispersing element 133 may be positioned within the stent cover 104 for drug dispersion. In one embodiment, the drug-dispersing element can be a spiral or helical microtubing 134 extending in a spiral or helical manner about one of the layers of the stent cover 104, the spiral microtubing comprising at least one venting opening 135 for drug dispersion. The microtubing may be made of a porous material, expanded PTFE, an elastic polymer, a tissue material, or collagen. The spiral microtubing 134 may further comprise an inlet port located outside of the chamber 106. A syringe 136 may be connected to the inlet port of the spiral microtubing for drug infusion. The drug-dispersing element may be characterized as a drug-permeable element.

The drug may be loaded into the cover 104 by injecting the drug (e.g., using the syringe 136) into the chamber 106 via the outer layer 110. Alternatively, the drug may be pre-loaded during fabrication. For example, if the cover 104 is made by mounting layers 108 and 110 sequentially over the stent 102, then after the inner layer 108 is mounted over the stent 102, the drug can be coated on to the surface of the inner layer 108 facing the chamber 106 (or the surface of the outer layer 110 facing the chamber 106) before the outer layer 110 is attached to the inner layer 108.

One or both layers 108, 110 can even be provided with one or more perforations 118, 137, 138, 139 to promote faster drug release by bypassing the normal drug diffusion process to provide a burst of drug concentration at a localized region. The number of perforations provided can be varied depending on the desired burst of concentration. For example, the ends 120, 122 of the stent 102 may benefit from an initial higher dosage of drug. When the prosthesis 100 is in its collapsed state during delivery, the perforations are closed (because of the flexible nature of the material for the cover 104), but are opened when the prosthesis 100 and its cover 104 are expanded.

Figures 7, 8:
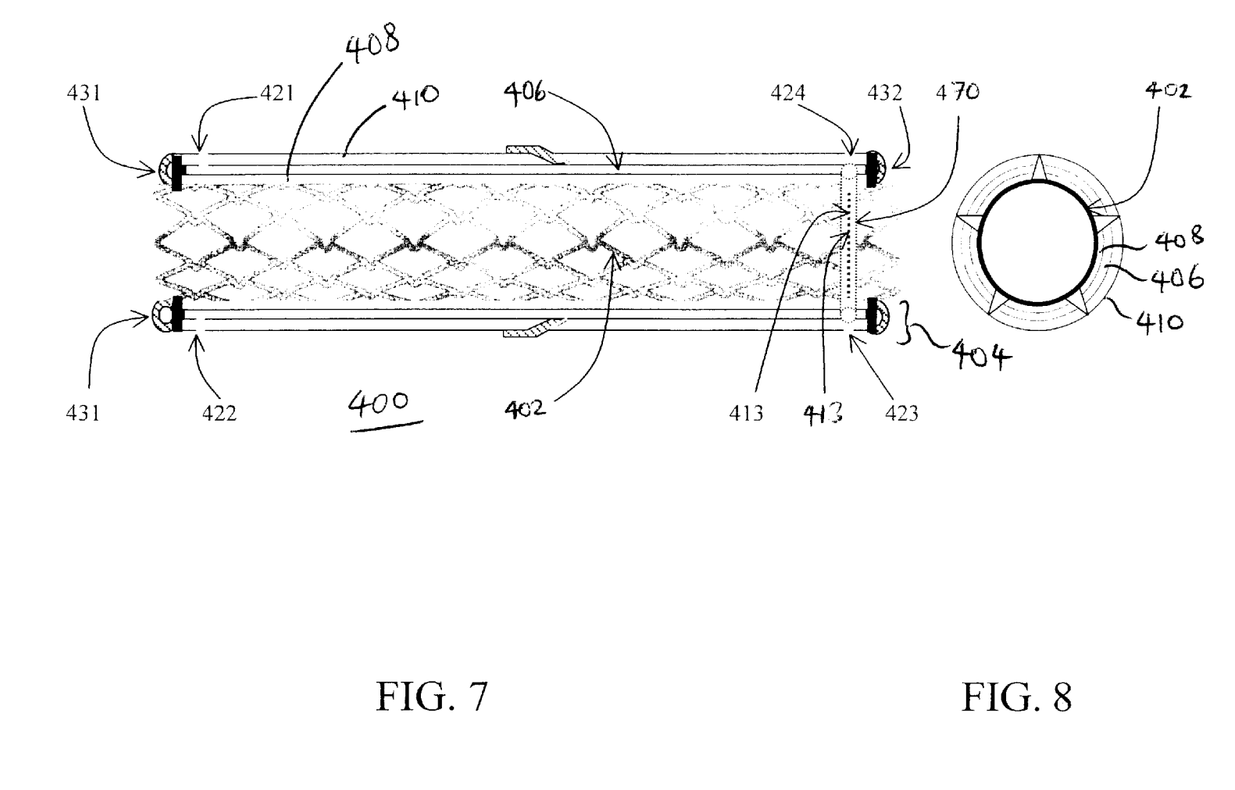
FIG. 7 is a schematic view of an intraluminal prosthesis according to yet another embodiment of the present invention.
FIG. 8 is a cross-sectional view of the prosthesis of FIG. 7.

The drug-dispersing element of the stent cover of the present invention may comprise a distributor ring. FIGS. 7 and 8 illustrate a stent cover 404 that has two opposing edges 431 and 432, and one or more perforations 421, 422, 423, 424. The stent cover 404 has one or more distributor rings 470 that can be positioned in the chamber 406 defined by the two layers 408 and 410 of the stent cover 404. The distributor rings 470 can be positioned at any location along the length of the stent cover 404. The stent cover 404 can be secured to the stent 402 (which can be the same as any of the stents 102, 202, 302 described above) using any of the techniques described above. Each distributor ring 470 can be made of a flexible material (e.g., such as but not limited to PTFE, ePTFE, PET, polyurethane, etc.), and has a plurality of venting openings 413 for dispersing drug(s) stored inside the distributor ring 470. Each distributor ring 470 may be used to deliver drugs to the chamber 406, and then removed from the chamber 406, before the prosthesis 400 is implanted inside an anatomical structure. Alternatively, the distributor ring 470 can be left inside the chamber 406 even after the prosthesis 400 has been implanted. Each distributor ring 470 can be removed from the chamber 406 by pulling it out of the stent cover 404 via one of the perforations 421, 422, 423 or 424.

The prosthesis 100 or 400 can be implanted using any known methods for the underlying stent 102. A catheter can be used to deliver the prosthesis 100 to the desired location in the vessel, and then the stent 102 can be expanded (i.e., either self-expanding or balloon expanded, depending on the type of stent). In essence, the prosthesis 100 or 400 will be deployed and used in the same manner as its underlying stent 102. The deployment techniques and functions of the stent 102 are well-known, and shall not be explained in greater detail herein.

As shown in FIG. 2, a specific looping suture 141 is provided to tighten the suture at the end 103 of the stent 102 for firmly securing the cover 104 onto the underlying stent 102. The mechanism for a looping suture and methods for tightening a looping suture is well known in the art.

Under certain circumstances, each material layer 108, 110 can be coated with an additional layer of tissue, hydrogel or polymer, depending on the surrounding parameters and desired application. For example, if a layer 108 or 110 is provided with a material that does not meet a desired parameter or requirement (e.g., porosity, structural strength, compatibility), an additional layer of tissue, hydrogel or polymer that does meet the desired parameter or requirement can be coated on to the layer 108 or 110 by (a) dipping the layer 108 or 110 into a solution of the coating (solution of tissue, polymer or hydrogel), (b) spraying the coating on to the layer 108 or 110, or (c) wiping the coating on to the layer 108 or 110.

Figure 3:
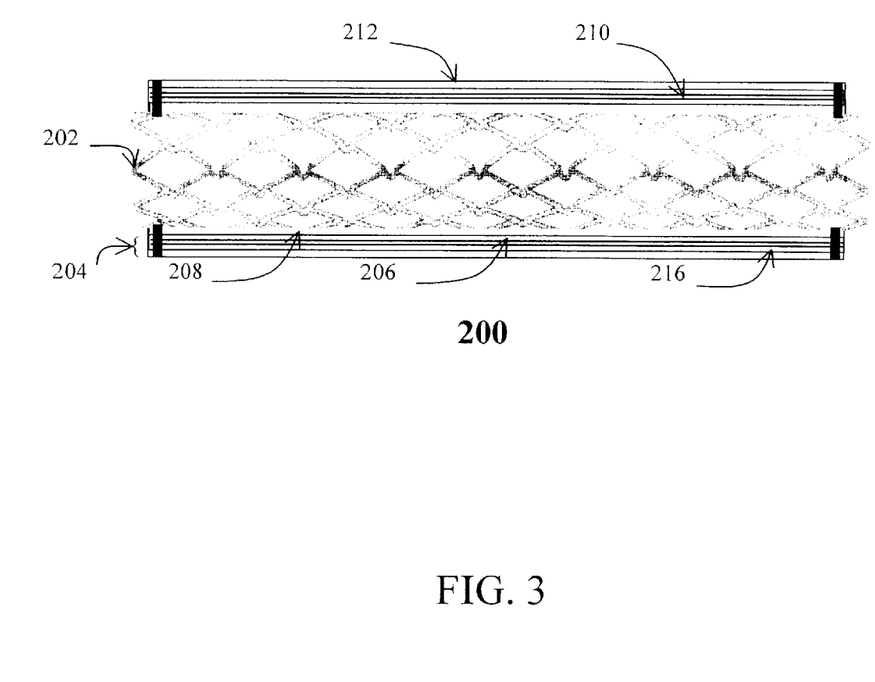
FIG. 3 is a schematic view of an intraluminal prosthesis according to another embodiment of the present invention.

In addition, the cover 104 can be comprised of more than two layers of materials. FIG. 3 illustrates a prosthesis 200 according to another embodiment of the present invention where the tubular stent 202 has a cover 204 attached over the outer periphery of the stent 202, with the cover 204 made up of three or more layers 208, 210, 212 of material to define two or more chambers 206 and 216. Each chamber 206 and 216 can be used to store the same or different drugs for delivery to different locations, as explained below. The stent 202 can be the same as stent 102, and the attachment methods described above can also be used to attach the cover 204 to the stent 202.

Figure 4:
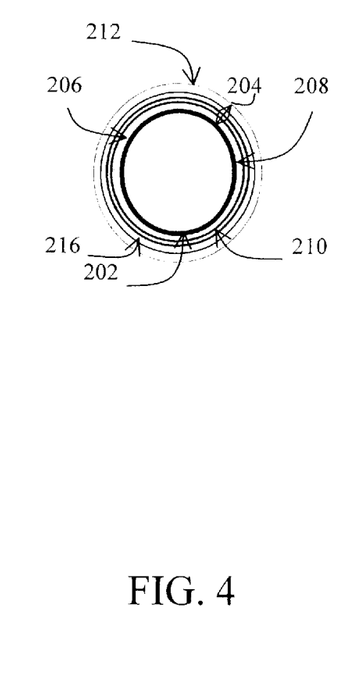
FIG. 4 is a cross-sectional view of the prosthesis of FIG. 3.

The inner layer 208 can function to allow drug diffusion therethrough to the stent 202 and internal passageway. The middle layer 210 can be used to separate the two drug chambers 206, 216, and if use for this purpose, should be impermeable to drugs and fluid. The outer layer 212 can function to allow drug diffusion therethrough to the diseased vessel wall. Similarly, the inner chamber 206 can be used to store drugs intended for delivery to the stent 202 and internal passageway, and the outer chamber 216 can be used to store drugs intended for delivery to the diseased vessel wall.

Figure 5:
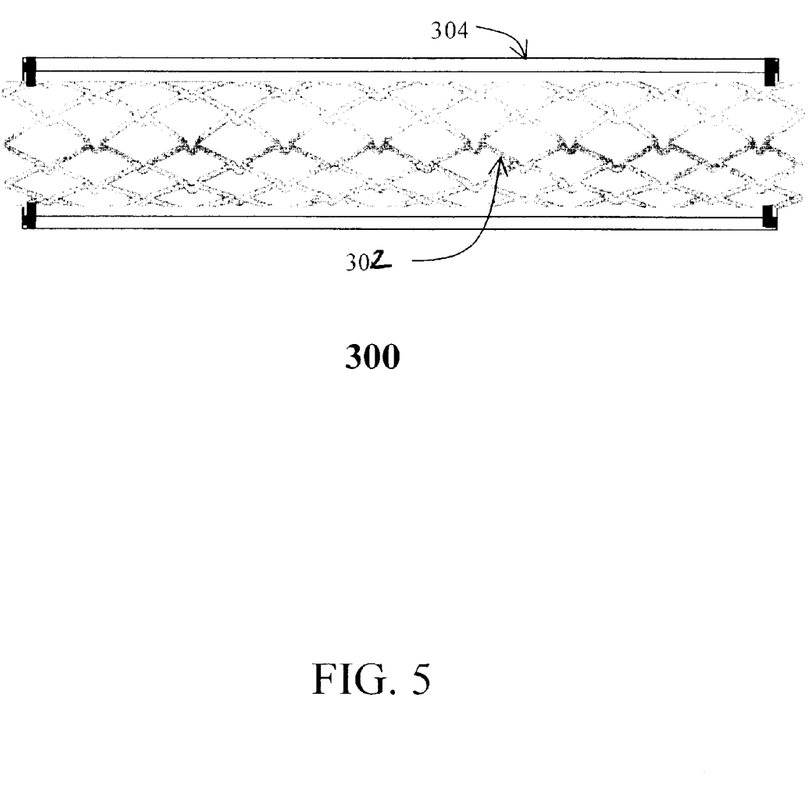
FIG. 5 is a schematic view of an intraluminal prosthesis according to yet another embodiment of the present invention.
Figure 6:
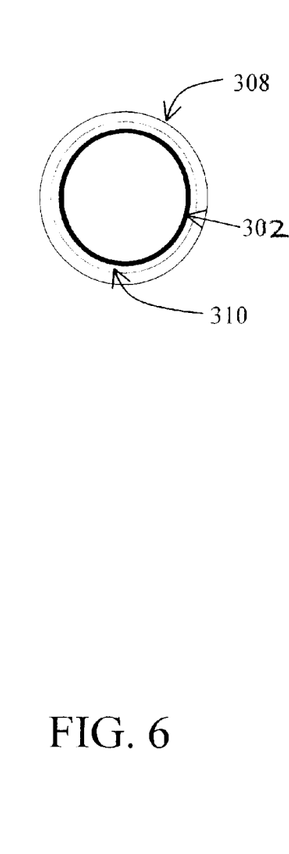
FIG. 6 is a cross-sectional view of the prosthesis of FIG. 5.

FIGS. 5 and 6 illustrate a further modification to the cover 104, which is embodied by a prosthesis 300 having a cover 304 positioned about a stent 302 in which the drug(s) are actually loaded on to at least one of the two layers 308 and 310 so that a chamber between the two layers 308, 310 is not needed. Each layer 308, 310 can be made from either tissue, hydrogel or polymer, and each layer 308, 310 can be loaded with different drugs or the same drugs with different dosages. The provision of the two or more drug-loaded layers 308, 310 provides better control for drug release, and allows two or more drugs to be delivered at the same time, or at the same time in different directions, or at different times. There are a number of ways of loading the drug(s) to the layers 308, 310 in the cover 304. The material utilized for the layers 308, 310 may have water content greater than 90% by weight. If so, the water can be removed by a lyophilization process that is a well-known technique in the art.

One method involves physical absorption into the layers 308, 310. Under this method, the drug is loaded into the material during the rehydration process. The drug may be dissolved in a physiological solution for rehydration of the lyophilized material. If the drug has limited solubility in water, additional solvent may be added to facilitate the dissolving process, as long as the solvent has no adverse effects on the cover and the host patient. As an example, ethanol at a concentration of less than 50% v/v may be suitable for the rehydration process. The rehydration process for tissue and hydrogel is fast, easy and complete. The material has no noticeable change in property before dehydration and after complete rehydration. By changing the hydrophilicity of the material, the drug may be released at different rates.

A second method involves the use of a charged chemical to electronically attract and retain drugs. In particular, natural tissue and certain hydrogels are proteins, which are composed of amino acids with various kinds of functional groups. By choosing the appropriate modification reagent, it is possible to selectively reduce certain groups to imbalance the surface and matrix charge of the tissue or hydrogel to either positive or negative. For example, aldehyde group will react with amino group to change the surface and matrix charge to negative. Carbodiimide reaction will target the free carboxyl group to change the surface and matrix charge to positive. Addition of charged chemicals into tissue may also change the net electricity of the tissue. A charged tissue or hydrogel material has the tendency to electronically attract and retain a drug carrying the opposite charge. The drug will then be released inside the vessel after implantation. The release of the drugs is accomplished by other charged particles in the patient's body which competes with the charged binding site in the hydrogel material for the drug.

A third method involves chemical reaction or bonding to link certain drugs to the material. The bonding may be covalent or ionic. For example, heparin may be immobilized to tissue surface covalently through direct Carbodiimide reaction or with polyethylene oxide as a bridge or spacer. Heparin can also link to tissue through ionic interaction through benzalkonium or stearylkonium. The drug may be released or remain on the surface of the tissue or hydrogel with activity in the vessel.

A fourth method involves coating the surface of the tissue or hydrogel. For example, the drug can be sprayed onto the surface, and then a gel-like material may be used to coat the tissue or hydrogel. As another example, it is also possible to first mix the gel with the drug, and then coat the mixture on to the material. As yet another example, the gel may be applied over the outer layer of the tissue or hydrogel before the drug is loaded. Then, just before implantation, the layer 308 or 310 can be immersed in a solution containing the drug, and the nature of the gel will cause the drug to be retained or loaded in the gel. The prosthesis 300 can then be delivered inside the desired vessel and the drug will be released over a period of time. Examples of the gel-like material can include polyethylene oxide, polyvinyl pyrrolidone, polyacrylates, and their blends or co-polymers or lightly crosslinked forms. Other examples include polyethylene glycol block copolymers with polylactides or other polyesters. Yet other examples include hydrophilic polyurethane, poly(maleic andydride-alt-ethylene) and their derivatives. Further examples include polysaccharides and their derivatives, sodium alginate, karaya gum, gelatin, guar gum, agar, algin, carrageenans, pectin, locust bean gums, xanthan, starch-based gums, hydroxyalkyl and ethyl ethers of cellulose, sodium carboxymethylcellulose. Some of these gel-like materials can be heated and then cooled to form the gel. Some are food gels and some are bioadhesives.

Figure 9:
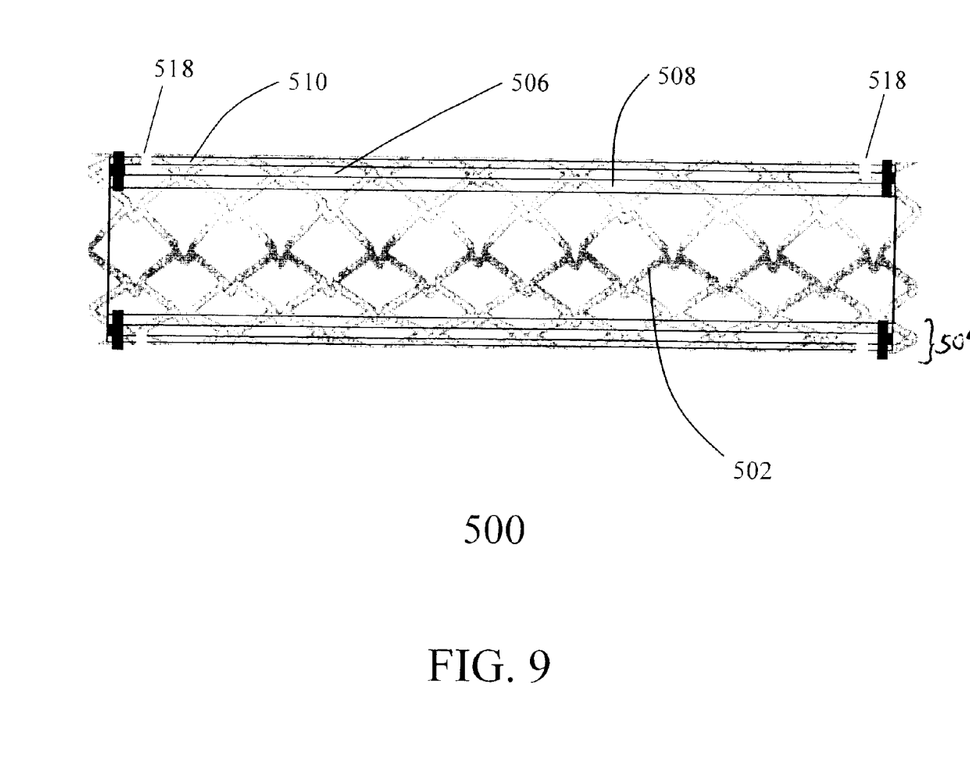
FIG. 9 is a schematic view of an intraluminal prosthesis according to yet another embodiment of the present invention.
Figure 10:
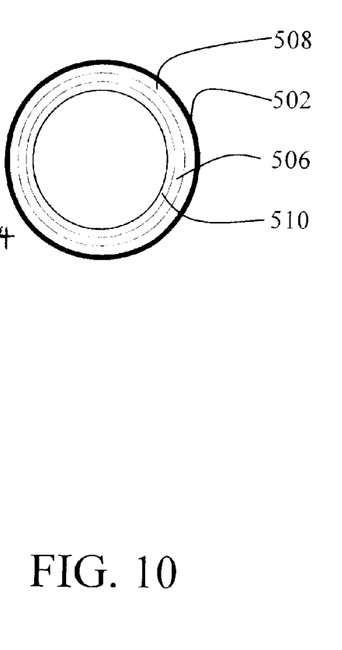
FIG. 10 is a cross-sectional view of the prosthesis of FIG. 9.

FIGS. 9 and 10 illustrate a prosthesis 500 according to another embodiment of the present invention where the stent cover 504 comprises two layers 508 and 510 that are positioned in the inner wall of the stent 502. The two layers 508 and 510 can be spaced to define a chamber 506 therebetween. One or more perforations 518 can be provided in one or both of the layers 508, 510. The stent cover 504 can be attached to the stent 502 using the same techniques and mechanisms described above for the other embodiments. Thus, the stent cover 504 is especially well-suited for several applications. First, the stent cover 504 can deliver drugs to the interior of the stent 502, such as delivering drugs to the blood flow of the patient. Second, the stent cover 504 is protected from damage when the stent 502 expands (e.g., when the stent 502 over-expands) during deployment inside a vessel. Third, certain stents 502 may have an outer surface that provide effective friction forces or mechanisms for anchoring the stent 502 to the luminal wall of the vessel, and the stent cover 502 being positioned inside the lumen of the stent 502 will ensure that the stent cover 502 does not detract from the effectiveness of the friction forces or anchoring mechanisms.

Figure 11:
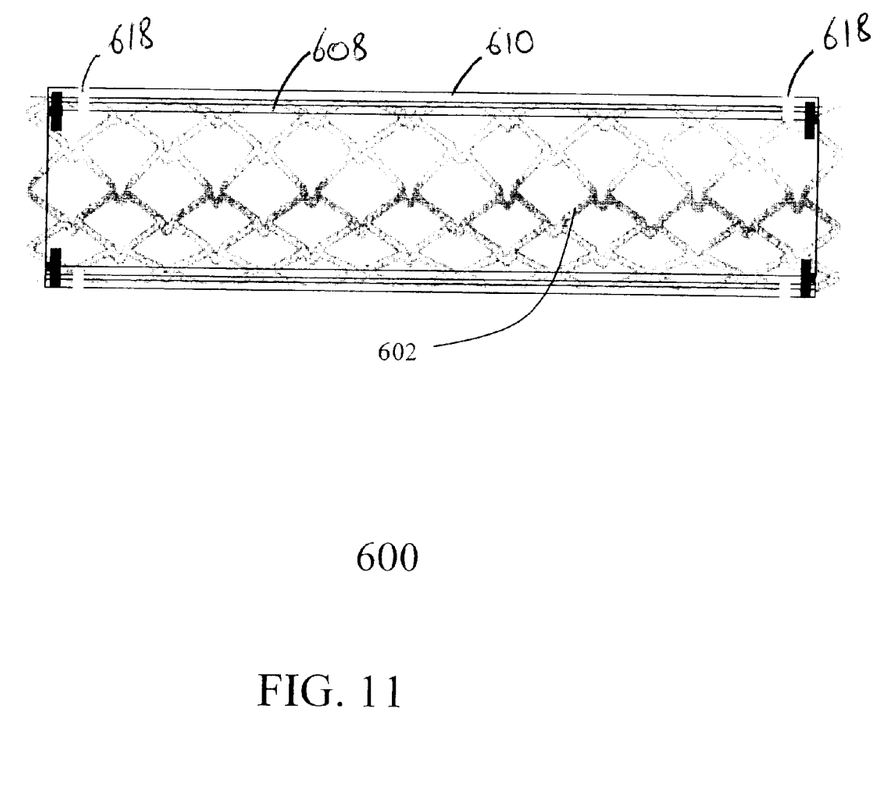
FIG. 11 is a schematic view of an intraluminal prosthesis according to yet another embodiment of the present invention.
Figure 12:
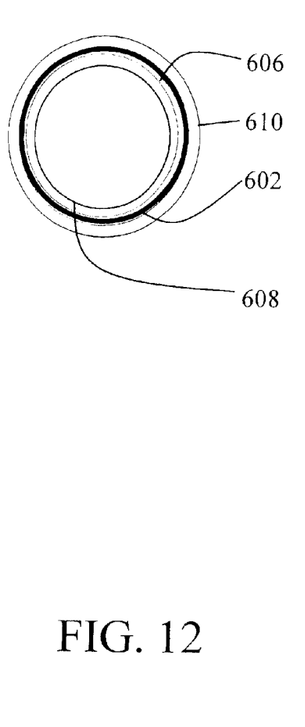
FIG. 12 is a cross-sectional view of the prosthesis of FIG. 11.

FIGS. 11 and 12 illustrate a prosthesis 600 according to another embodiment of the present invention where the stent cover 604 comprises two layers 608 and 610 that are spaced to define a chamber 606 therebetween. The stent 602 is retained inside the chamber 606. One or more perforations 618 can be provided in one or both of the layers 608, 610. The stent cover 604 can be attached to the stent 602 using the same techniques and mechanisms described above for the other embodiments. Thus, the stent cover 604 is especially well-suited for applications where the vessel has a very small diameter (e.g., neuro-vascular vessels, among others), since the profile of the entire prosthesis 600 is minimized given the fact that the stent 602 is retained inside the chamber 606.

Thus, the covers 104, 204, 304, 504, 604 of the present invention provide a sheath or sleeve to block the path of cell migration (i.e., ingrowth), and to pave or act as a scaffold for supporting the lumen. The covers 104, 204, 304, 504, 604 act as effective drug delivery devices for locally delivering a drug to an arterial wall or lumen into which the prosthesis 100, 200, 300, 500, 600 has been inserted and positioned. The covers 104, 204, 504, 604 also provide, in some embodiments, a chamber 106, 206, 506, 606 that can store and slowly release the desired drug in a controlled manner.

The stent and stent cover of the present invention may be used for stenting body passageways (e.g., esophagus, bile duct, trachea, intestine, vasculature and urethra, among others) to hold open passageways which have been blocked by cancerous material growth or tumors. More particularly, the stent cover can be provided about the outer periphery or the inner periphery of the stent, with the stent cover having at least two layers of materials to define at least one chamber therebetween that is sealed at all edges. A radioactive material may be optionally placed within the sealed chamber for intended radiotherapy. The method of sealing the chambers may include gluing, stitching, adhering, stapling, suturing, heat fusion, ultrasound welding, impedance welding, or other appropriate mechanisms as disclosed in the present invention. When used in this application, the layers of materials can be made of biocompatible synthetic polymer, such as polyurethane, silicone, silicone-polyurethane copolymer and fluoro-containing polymer.

EXAMPLE 1

The cover 104 is formed of two layers of material. 1 mg of Eleutherobin is loaded into the chamber 106, and the material of the two layers 108 and 110 are then lyophilized. Because of higher incidence of problems at the two ends 120, 122 of the stent 102, more rapid drug release at the ends 120, 122 is desired. Six 2 micron holes are created at each end 120, 122 on the outer layer 110, so that each hole opens to 10 microns upon rehydration and deployment. These holes facilitate faster release of the drug.

EXAMPLE 2

Flexible polyurethane forms the outer layer 110 and porous polyurethane forms the inner layer 108 of the cover 104. The edges of the two layers 108, 110 are sealed, and heparin (low molecular weight heparin loaded at 100 unit/cover) is loaded. Heparin is only released to the internal passageway.

EXAMPLE 3

Expandable PTFE forms the outer layer 110, which is sealed with polyurethane. This outer layer 110 is not drug permeable. The inner layer 108 is made of a porous ePTFE. The two layers 108, 110 are sealed at high temperature. 5 ug of Antithrombin D-Phe-Pro-Arg Chloromethy ketone (PPACK) are loaded to the chamber 106. The drug is gradually released to the internal passageway.

Vulnerable Plaque

To varying degrees, an atheromatous lesion is comprised of a lipid-rich core, a cap of fibrous tissue, vascular muscle cells expressing collagen and elastin that impart tensile strength to an extracellular matrix, and inflammatory cells that produce various enzymes and procoagulant factors. For illustration purposes in the present invention, an atherosclerotic plaque is generally divided into two categories: a vulnerable plaque and a stable plaque. A stable plaque is generally characterized by the most conspicuous stenoses, that is, the angiographically significant (greater than 70% diameter narrowing) lesions versus a large number of insignificant (less than 50% diameter narrowing) unapparent lesions (called vulnerable plaque).

After angioplasty on a stable plaque, a stent is typically implanted intraluminally. The pressure to deploy a stent by an expandable balloon is generally in the range of 6–10 atmospheres or higher. The stent and its stent cover for use in treating a stable plaque functions to maintain the lumen dimension and prevent stent restenosis. The device should be very strong circumferentially, but there will be no requirement for longitudinal strength.

On the other hand, a vulnerable plaque has little luminal narrowing and cannot be imaged angiographically. The fibrous cap, which is characterized by a single endothelial cell layer, may be thinned and partially eroded by both inflammatory T-lymphocytes and invading smooth muscle cells. Abundant activated macrophages moving into the plaque from the vasa vasorum produce proteolytic enzymes, such as matrix metalloproteinases, that promote collagen degradation, which leads to cap disruption and the thrombogenic surface activation associated with acute coronary syndromes.

The covers 104, 204, 304, 504, 604 of the present invention are not only useful in treating the restenosis of a stable plaque, but can also be used to treat or prevent the rupture or erosion of a vulnerable plaque.

An endoluminal cover (e.g., 104, 204, 304, 504, 604) or patch to cover the vulnerable plaque can be supported by a supporting element, such as a low pressure stent like any of the stents illustrated hereinabove. The supporting element holds the covering material of the cover against the luminal wall of the vessel to prevent the rupture of the vulnerable plaque. There should be little pressure or circumferential force exerted from the supporting element onto the cover or patch, and against the luminal wall of the vessel. The vulnerable plaque is a lesion inside the vessel wall having a morphology where the vulnerable plaque does not protrude into the lumen of a blood vessel. Therefore, there is no need to push radially outwardly or to stent the vulnerable plaque. However, to assure that the stent cover or patch stays on top of a vulnerable plaque, the supporting element is needed at least on a temporary basis.

In general, the circumferential force should be uniformly distributed around the outer periphery of a stent or supporting element. The term "circumferential force" as used herein is intended to mean the force to hold the stent in place at about the lesion region by most of the stent structure, whose holding force is employed against the blood flow and any other hemodynamic or physiological effects on the stent. The "radial force" of a stent as used in the present invention is intended to mean a force at one or more portions of the stent used to treat a stable plaque that is usually non-uniform and non-homogeneous. The radial force to treat a stable plaque is large and is adapted to break out the calcified or solidified atherosclerotic plaque, so that the radial force is generally in the 10 to 15 atmosphere pressure range. Typically, after the stable plaque is broken out, the circumferential force to hold a stent in place for treating stable plaque is believed to be about 10 to 150 mm Hg (absolute), preferably 10–50 mm Hg. It is also noted that the typical diastolic pressure is 80 mm Hg and the systolic pressure is typically 120 mm Hg for a healthy person when treating stable plaque.

The circumferential force for a stent cover that is used for vulnerable plaque should only be sufficient to hold the stent cover along with its supporting element. Therefore, the circumferential force of a stent for treating vulnerable plaque should be less than the radial force needed for treating a stable plaque. If the radial force of a stent cover for treating vulnerable plaque is too large, then the vessel wall might be pushed outwardly to cause false aneurysms.

Figures 13, 14:
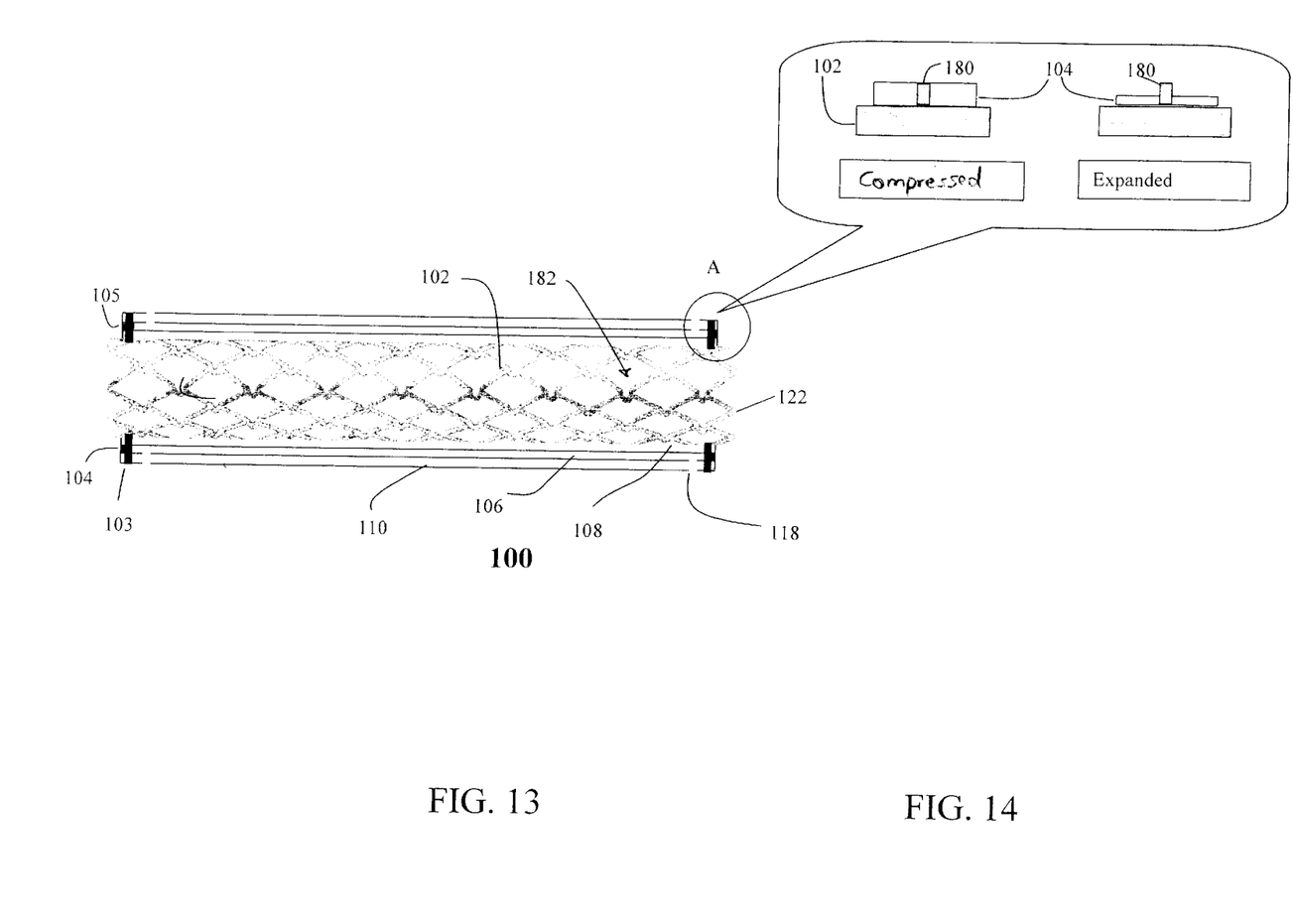
FIG. 13 is a schematic view of the prosthesis of FIG. 1 illustrating certain modifications made thereto.
FIG. 14 is an expanded cross-sectional view of the section labeled A in FIG. 13.

Another method for holding the stent cover or patch in place in the vessel can include "frictional force" exerted by the exterior surface of the stent cover or patch to the luminal wall of the vessel. As is known, a rough surface has higher friction (under the same circumferential force scenario) to hold the stent cover in place. Therefore, the stent and stent cover combination of the present invention can include a micro-level rib, protrusion, or wavey, or studded cover surface after deployment to increase the surface friction between the cover and the contacted tissue. As shown in FIGS. 13 and 14, an anchoring mechanism 180 (e.g., a rib, a protrusion, or even a wavy or studded configuration) can extend from the structure of the stent 102. The anchoring mechanism 180 can extend through the material of the stent cover 104 (if necessary) before the stent 102 is expanded, and exposed through the outer wall of the stent cover 104 to help anchor the stent cover 104 to the vessel wall when the material of the stent cover 104 is stretched upon deployment of the prosthesis 100.

Another way to hold the stent cover or patch in place in the vessel is to employ the stent structure itself. A stent particularly useful for this vulnerable plaque application can have a stent cell size of 0.05 to 0.25 mm during its compressed or non-deployment state and be enlarged to 0.5 to 2.5 mm after deployment or expansion. At the time the stent is deployed or expanded, the stent cell size, shape and outer contour of certain stents may change significantly from those in the compressed or non-deployment state. Depending on the design of the underlying stent, the larger stent cell size and changed outer contour may provide the stent cover with greater undulation (i.e., rougher or more uneven) to facilitate better anchoring onto the tissue surface of a vulnerable plaque. For example, the cells 182 of the stent 102 should be small enough to yield a uniform force distribution on the luminal wall of the vessel. In other words, the circumferential force for holding a stent with its cover covering the vulnerable plaque in place for treating vulnerable plaque is believed in the range of a few mm Hg, which is less than the circumferential force utilized for stenting a region having stable plaque. Similarly, the maximum wire to wire distance (or the equivalent diameter of the cell area as defined as the circumference divided by pi) within a stent 102 should not be more than 3 mm.

The stent cover used for a vulnerable plaque may be less stretched as compared to stent covers used for the stable plaque because (i) the vulnerable plaque does not need excess radial force, and (ii) it is not necessary to expand the stent 102 as much as when treating a stable plaque because a stable plaque has stenosis which protrudes into the vessel lumen, while vulnerable plaque does not have any stenosis. Thus, when used to treat vulnerable plaque, the stent cover functions to provide a scaffold for containing the vulnerable plaque from rupturing or eroding. Additional steps to further secure the stent cover to the vulnerable plaque area may include applying adhesives, local polymerization, and physical energy (e.g., laser, heat) to fuse the stent cover to the wall of the vessel.

A stent cover can also be loaded with drug(s) (using the techniques described above) that are effective in preventing, slowing down or even reversing the vulnerable plaque process. A site-specific drug therapy with a stent cover can be critical and beneficial for vulnerable plaque treatment.

The present invention also provides a method for treating a vulnerable plaque. According to this method, a drug can be loaded into a stent cover 104 using the techniques described above, and the stent cover 104 is delivered to the location of the vulnerable plaque. The cover 24 is internally supported by a supporting element, which may comprise an expandable stent 102. The stent 102 and the cover 104 are expanded in the vessel to cover the vulnerable plaque. The cover 104 can surround an outer periphery of the stent 102, and can comprise at least one layer of material (or even two or more layers of materials), as described above. In particular, the over 104 extends along at least a portion of, or the complete length of, the stent 102.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A prosthesis, comprising:

a stent having an outer periphery;

a cover provided about the outer periphery of the stent, the cover comprising at least two layers of materials, with at least one layer of material being permeable to drugs; and a drug dispersing element coupled to the cover.

2. The prosthesis of claim 1, wherein the at least two layers of materials defines at least one chamber therebetween.

3. The prosthesis of claim 2, wherein the drug dispersing element is a microtubing that is positioned inside the at least one chamber.

4. The prosthesis of claim 1, wherein at least one of the layers has at least one perforation.

5. The prosthesis of claim 1, wherein one of the layers is impermeable to drugs.

6. The prosthesis of claim 1, wherein the drug dispersing element is a distributor ring positioned around the stent, the distributor ring having a plurality of venting openings.

7. The prosthesis of claim 1, wherein the drug dispersing element is a microtubing that extends along the cover, the microtubing having a plurality of venting openings.

8. The prosthesis of claim 1, wherein the drug dispersing element is removable from the cover.

9. A prosthesis, comprising:

a stent having an inner periphery that defines a lumen;

a cover provided about the inner periphery of the stent, the cover comprising at least two layers of materials that are positioned inside the lumen of the stent, with at least one layer of material being permeable to drugs; and a drug dispensing element courled to the cover.

10. The prosthesis of claim 9, wherein the at least two layers of materials defines at least one chamber therebetween.

11. The prosthesis of claim 9, wherein one of the layers has at least one perforation.

12. A prosthesis, comprising:

a stent having an inner periphery that defines a lumen; and a cover provided about the inner periphery of the stent, the cover comprising at least two layers of materials that are positioned inside the lumen of the stent, with at least one layer of material being permeable to drugs.

13. A prosthesis, comprising:

a stent;

a cover that extends across a portion of the stent, the cover comprising at least two layers of materials that are completely sealed to define at least one chamber therebetween; and a radioactive material provided inside the at least one chamber.

14. The prosthesis of claim 13, wherein the stent has an inner periphery that defines a lumen, and wherein the cover is provided inside the lumen adjacent the inner periphery of the stent.

15. The prosthesis of claim 13, wherein the at least two layers of material are selected from the group consisting of: polyurethane, silicone, silicone-polyurethane copolymer, and fluoro-containing polymer.

\* \* \* \* \*